United States Patent [19]

Lippman

[11] Patent Number: 4,695,590

[45] Date of Patent: Sep. 22, 1987

[54] METHOD FOR RETARDING AGING

[75] Inventor: Richard D. Lippman, Scottsdale, Ariz.

[73] Assignee: California Health Technologies, Los Angeles, Calif.

[21] Appl. No.: 859,464

[22] Filed: May 5, 1986

[51] Int. Cl.[4] .......................................... A61K 31/045
[52] U.S. Cl. ................................................... 514/724
[58] Field of Search ........................................ 514/724

[56] References Cited

U.S. PATENT DOCUMENTS 2,644,822  7/1953  Pearl .................................. 260/240.9
3,934,034  1/1976  Manning ............................. 424/346
4,530,844  7/1985  Smerbeck et al. .................. 514/458

OTHER PUBLICATIONS

A. Comfort et al., "Effect of Ethoxyquin on the Longevity of C3H Mice", Nature, Jan. 22, 1971, vol. 229, No. 5282.
Kenneth D. Munkres et al., "Ageing of Neurospora Crassa I. Evidence for the Free Radical Therory of Ageing from Studies of a Natural-Death Mutant", Mechanisms of Ageing and Development, 5 (1976) 79-98.
Simion Oeriu et al., "The Effect of the Administration of Compounds which Contain Sulfhydryl Groups on the Survival Rates of Mice, Rats, and Guinea Pigs", Journal of Gerontology, Jul. 1965, vol. 20, No. 3.
Neal K. Clapp et al., "Effects of the Antioxidant Butylated Hydroxytoluene (BHT) on Mortality in BALB/c Mice[1]", Journal of Gerontology, Jul. 1979, vol. 34, No. 4.
Nobuhiro Morisaki et al., "Fatty Acid Metabolism and Cell Proliferation V. Evaluation of Pathways for the Generation of Lipid Peroxides", LIPIDS, vol. 19, No. 6 (1984).
A. E. Economos et al., "Accelerated Aging of Fasted Drosophila", Experimental Gerontology, vol. 17, No. (1982).
Denham Harman, "Free Radical Theory of Aging: Effect of Free Radical Reaction Inhibitors on the Mortality Rate of Male LAF Mice[1]", Journal of Gerontology, Oct. 1968, vol. 2-3, No. 4.
Jaime Miquel et al., "Favorable Effects of the Antioxidants Sodium and Magnesium Thiazolidine Carboxylate on the Vitality and Life Span of Drosophila and Mice", Experimental Gerontology, vol. 14, No. 5, 1979.
Denham Harman, "Prolongation of the Normal Lifespan and Inhibition of Spontaneous Cancer by Antioxidants", Journal of Gerontology, Jul. 1961, vol. 16, No. 3.
Kenneth D. Munkres et al., "Ageing of Neurospora Crassa II. Organic Hydroperoxide Toxicity and the Protective Role of Antioxidant and the Antioxygenic Enzymes", Mechanisms of Ageing and Development, 5 (1976).
Kenneth D. Mondres et al., "Ageing of Neurospora Crassa VII. Accumulation of Fluoroescent Pigment (Lipofuscin) and Inhibition of the Accumulation by Nordihydroguaiaretic Acid", Mechanisms of Ageing and Development, 7 (1978).

Primary Examiner—Stanley J. Friedman
Attorney, Agent, or Firm—Christie, Parker & Hale

[57] ABSTRACT

Methods and compositions are provided for retarding aging, i.e., inhibiting damage to human cells caused by toxic byproducts of oxygen metabolism. The anti-aging active ingredient is a compound or mixture of compounds represented by the following structural formula:

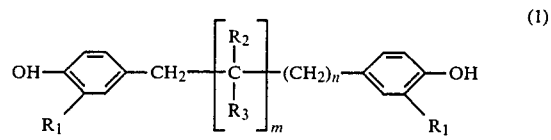

wherein
m is 0, 1 or 2;
n is 0 or 1;
R1 is hydrogen, halogen or hydroxy; and
R2 and R3 each independently represent hydrogen or methyl provided that when m is 0, n is 0 and when m is 1 or 2, n is 1 and R1 is hydroxy or halogen and that when m is 2, each R2 can be the same or different and each R3 can be the same or different or a pharmaceutically acceptable alkali or alkaline earth metal salt thereof.

16 Claims, 4 Drawing Figures

Kenneth D. Mondres, "Antioxidants Prolong Life Span and Inhibit the Senescence-Dependent Accumulation of Fluorescent Pigment (Lipofuscin) in Clones of Podospora Anserina", *Mechanisms of Ageing and Development,* 7 (1978).

Richard D. Lippman, "Rapid in Vivo Quantification and Comparison of Hydroperoxides and Oxidized Collagen in Aging Mice, Rabbits and Man", *Experimental Gerontology,* vol. 20, 1985.

Richard D. Lippman, "Chemiluminescent Measurement of Free Radicals and Antioxidant Molecular-Protection Inside Living Rat-Mitochondria", *Experimental Gerontology,* vol. 15, 1980.

Horrum et al., "Free Radical Theory of Ageing: Effect of Antioxidant on Mitochrondira", University of Nebraska College of Medicine and VA Medical Center, Omaha, Nebr.

J. Epstein et al., "Studies on Ageing in Nematodes IV. The Effect of Antioxidants on Cellular Damage and Life Span", *Mechanism of Ageing and Development,* vol. 1, 1972.

Robert R. Kohn, "Effect of Antioxidants on Life-Span of C57BL Mice[1]", *Journal of Gerontology,* vol. 26, No. 3, 1971.

Simion Oeriu et al., "The Effect of the Administration of Compounds which Contain Sulfhydryl Groups on the Survival Rates of Mice, Rats, and Guinea Pigs".

Robert Bolla et al., "Age Dependent Changes in Enzymes Involved in Macromolecular Synthesis in Turbatrix Aceti", *Archives of Biochemistry and Biophysics,* vol. 169, 1975.

Denham Harman, "The Ageing Process", *Proceeding of the National Academy of Sciences,* vol. 78, No. 11, Nov. 1981.

S. V. Lieberman et al., "A Synthesis of Nordihydroguaiaretic Acid", *Journal of the American Chemical Society,* Jan.-Jun. 1947, vol. 69, pp. 1540-1541.

METHOD FOR RETARDING AGING

FIELD OF THE INVENTION

This invention relates to methods useful for retarding senescence or aging in mammals. In particular this invention relates both to methods for systemic treatment of humans with compositions comprising hydroxy substituted diphenylalkyls to inhibit damage to cells which causes aging and to methods for topical treatment of humans with compositions comprising hydroxy substituted diphenylalkyls, e.g., to inhibit damage to cells which causes wrinkling/aging of the skin.

BACKGROUND OF THE INVENTION

Actuaries define senescence as the increased likelihood of dying, but the appropriate pathological definition is progressive, multi-system organ atrophy. This is obviously not atrophy of disuse but atrophy of what can be called "cell drop-out". "Cell drop-out" as used herein means the disappearance of cells and consequent shrinkage of the body's organs. Such organ shrinkage is seen in autopsies on the aged. For example, the human brain can decrease from an average weight of 1,500 grams in a young human adult to a 1,000 grams or less in a human of advanced age. A brain that has decreased in size (the senescent brain) is highly forgetful, is unable to memorize new information and cannot react quickly to external stimulae. Shrinkage with age is also found in other human organs such as the heart, liver, kidneys, lymph nodes, skeletal muscles and vertebrae. Such shrinkages often correspond to the accumulation of peroxidized, free radical products seen as brown-yellow age pigment (lipofuscin). Other corresponding changes that are associated with aging are wrinkled skin, depleted fat deposits, fewer dermal melanocytes, brittle bones, low infection resistance, poor exercise tolerance and lack of reproductive ability.

At the cellular level, senescence means inadequate DNA repair leading to disordered and/or nonexistant cell replication, loss of mitotic control factors in the nucleous and cytoplasm including disordered nuclear-cytoplasmic exchange, and permanent closing of microcirculatory capillary beds resulting in focal cell drop-out and loss of cell and organelle membrane function. This progressive cellular process affects all organs and tissues throughout the body and its etiology and pathogenesis must therefore involve a universal and fundamental aspect of cell physiology.

Aging of the mammalian organism as a whole must be examined at the cellular level because changes of individual cells affect changes in individual body organs and changes in individual body organs affect the organism as a whole. For example, death or dysfunction of a critical bodily organ, such as the heart, will result in the death of the body as a whole.

In any study on aging two distinct types of cells must be considered; normally dividing cells and postmitotic cells. Normally dividing cells are those of the skin, hair and gastrointestinal tract, for example. While thousands of such cells die daily, they are continually replaced. Their replacement is with nearly exact replicas until the time of aging or senescence begins. This time begins in the mid-twenties in man. The second cell type, i.e. post-mitotic cells, are those that make up the heart, brain and central nervous system, for example. Generally speaking, post-mitotic cells don't divide or reproduce. Mammals are born with a fixed number of post-mitotic cells which lose function and die daily throughout a mammal's life span. Death of a mammal occurs when a critical number of post-mitotic cells lose function or die in a critical organ, e.g. the brain.

Recent biomedical gerontological research has provided some theories regarding the metabolic course of events which leads to the ineviable loss of function, deterioration, destruction and death of mammalian cells. One convincing theory relates to mammalian cellular metabolism's reliance on oxygen metabolism. By "oxygen metabolism" is meant the burning of oxygen in the cells energy factories (mitochondria) together with foods such as fatty acids to produce adenosine triphosphate (ATP), the cell's energy source. Production of ATP occurs continually through enzymatically controlled chemical reactions. Unfortunately, these chemical reactions are not 100% efficient. For example, in the bacteria, E-coli, these reactions are only approximately 84% efficient. As one moves up the scale of evolution, these reactions become increasingly more efficient. In man the reactions are $94\pm2\%$ efficient.

More efficient "oxygen metabolism" in man as compared to other mammals results in a decrease in the burning rate of oxygen in man compared to other mammals, a decrease in the burning rate of fatty acids and carbohydrates, a decrease in the formation of toxic oxygen byproducts and a decrease in the temperature set-point of the body to below that of other mammals.

Even though the relative amount of byproducts produced by "oxygen metabolism" in man is less than the amount of such byproducts produced in other mammals, such byproducts are highly toxic. Examples of these toxic byproducts are the superoxide ($O_2^-$.) and hydroxyl (.OH) radicals. To illustrate the extreme toxicity of these radicals consider the following: When superoxide is mixed with water, concentrated hydrogen peroxide (an oxidative byproduct) is formed. Concentrated hydrogen peroxide poured onto the skin will damage it within a few minutes to a necrotic, sickly white appearance. The same chemical reactions occur inside mammalian, oxygen-burning cells. Although protective enzymes destroy hydrogen peroxide continually, such defenses are not 100% efficient. Thus, chemical destruction of cells can result. Since man consumes many pounds of oxygen daily, even a slight inefficiency in the use of oxygen resulting in the $O_2^-$. or .OH radicals and oxidative byproducts is significant. As used herein "toxic byproducts of oxygen metabolism" includes radicals such as superoxide ($O_2^-$.) and hydroxyl (.OH) as well as oxidative products produced by such radicals such as hydrogen peroxide and the like.

An example of cell damage caused by the byproducts from oxygen reactions, i.e. by toxic byproducts of oxygen metabolism, is damage to a cell's genetic material, DNA. It is known that approximately 7,000 DNA "hits" by toxic byproducts of oxygen metabolism occur daily in man. Fortunately, most of these are repaired enzymatically by the cells. It is known, however, that some cells that are not repaired may become cancerous.

Of the two previously described cell types, i.e. the normally dividing cells and post-mitotic cells, normally dividing cells are able to reproduce and replace damaged cells. Post-mitotic cells, on the other hand, while they are sometimes repaired after bombardment with toxic oxygen byproducts of oxygen metabolism, most often such bombardment reduces their function, damages their DNA and/or kills them outright. This is a steady-state, linear aging process until damage to DNA and cellular defensive enzymes becomes so great that the aging process acquires an endogenous, accelerating character.

The long term, lifetime effects of this endogenous toxic chemical bombardment can also be exemplified in the wrinkling and hardening of the skin and arteries with age. The skin and arteries consist of supportive material called collagen and elastin. Collagen is the major protein of the white fibers of connective tissue, cartilage and bone. Elastin, or elastic tissue, is the major connective tissue protein of elastic structures such as the large blood vessels and the skin. Elastin enables these structures to stretch, and then resume their orignal shape and size.

Collagen and elastin contain fibers internally linked together by chemical bonds called a "imide bonds". It is theorized that mammalian aging involves the oxidation of these imide bonds to "amide bonds". In the skin and arterial collagen and elastin of mammals, as more and more amide bonds are formed, the collagen and elastin fibers become increasingly less elastic and flexible. In man, it is known that these fibers harden at a rate of approximately 7% per decade after the age of maturity (approximately mid-twenties). This means that the arterial-vascular system has a theoretical life span of approximately 140 years before becoming 100% rigid.

Free radical pathology mechanisms seem to be involved at key points in the etiology and pathogenesis of cancer, occlusive atherosclerosis and wrinkling of the skin. Free radical pathology ensues largely from free radical and oxidation products which negatively affect cell membranes, collagen, elastin, immune functions, micro-circulation, nucleic acids and regulatory proteins. Scientific studies have shown that this mechanism progresses from inciting factors to free radical pathologic reactions to products to damage to organelles, cells and tissues resulting in aging and disease. Aging seems to simultaneously affect all cells, tissues and organs throughout the body in an insidious, progressive pattern whose pathogenesis and etiology therefore are thought to involve a fundamental and universal aspect of cell physiology.

The clinical significance of toxic free radicals and oxidative agents generated endogenously in living cells has been documented in various scientific, medical publications. An association between these toxic agents and aging has been observed.

It is therefore desired that methods be provided for inhibiting aging caused by free radicals and oxidative agents produced in living cells. Such methods desirably include systemic treatment of humans to inhibit aging of the entire body as well as topical treatment, e.g., to inhibit wrinkling/aging of the skin.

SUMMARY OF THE INVENTION

The present invention is directed to methods and compositions useful for retarding aging in humans, i.e., inhibiting damage to human cells caused by toxic by-products of oxygen metabolism. One embodiment of the present invention comprises administering to a human a daily dosage of from about 0.5 mg per kilogram of body weight to less then about 2 mg per kilogram of body weight of a pharmaceutically acceptable composition comprising a compound or mixture of compounds represented by the following structural formula:

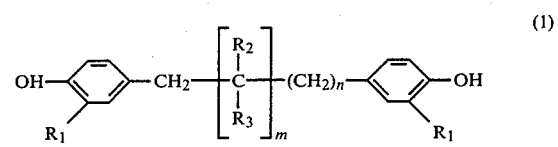

wherein
m is 0, 1 or 2;
n is 0 or 1;
R1 is hydrogen, halogen or hydroxy; and
R2 and R3 each independently represents hydrogen or methyl provided that when m is 0, n is 0 and when m is 1 or 2, n is 1 and R1 is hydroxy or halogen and that when m is 2, each R2 can be the same or different and each R3 can be the same or different or a pharmaceutically acceptable alkali or alkaline earth metal salt thereof.

Another embodiment of this invention is directed to methods and compositions for inhibiting wrinkling of the skin in a human by topically administering to the skin of such a human a pharmaceutically acceptable composition containing an effective amount of a compound or mixture of compounds represented by the following structural formula to inhibit wrinkling:

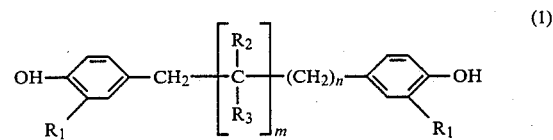

wherein
m is 0, 1 or 2;
n is 0 or 1;
R1 is hydrogen, halogen or hydroxy; and
R2 and R3 each independently represents hydrogen or methyl provided that when m is 0, n is 0 and when m is 1 or 2, n is 1 and R1 is hydroxy or halogen and that when m is 2, each R2 can be the same or different and each R3 can be the same or different or a pharmaceutically acceptable alkali or alkaline earth metal salt thereof.

In yet other embodiments of the present invention there are disclosed methods and compositions for inhibiting the formation of amide bonds in human collagen and elastin. One such method includes topically administering to the skin of such a human a pharmaceutically acceptable composition comprising an amount of a compound or mixture of compounds represented by the following structural formula sufficient to inhibit amide bond formation in human collagen or elastin:

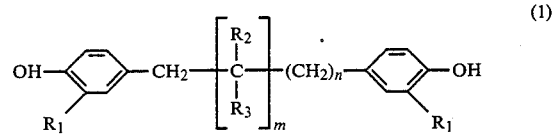

wherein
m is 0, 1 or 2;
n is 0 or 1;
R1 is hydrogen, halogen or hydroxy; and
R2 and R3 each independently represents hydrogen or methyl provided that when m is 0, n is 0 and when m is 1 or 2, n is 1 and R1 is hydroxy or halogen and that when m is 2, each R2 can be the same or different and each R3 can be the same or different or a pharmaceutically acceptable alkali or alkaline earth metal salt thereof.

BRIEF DESCRIPTION OF THE DRAWINGS

These are the features, aspects and advantages of the present invention will be more fully understood when considered with respect to the following detailed description, appended claims, and accompaning drawings, wherein:

DETAILED DESCRIPTION

Figure 1:
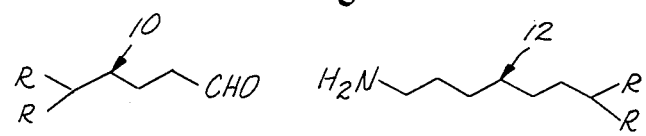
FIG. 1 is a schematic representation of two collagen fibers (R) or of two elastin fibers (R) lying side by side, showing a reversible imide bond linking them together.
Figure 1:
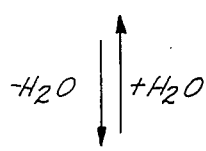
Figure 1:
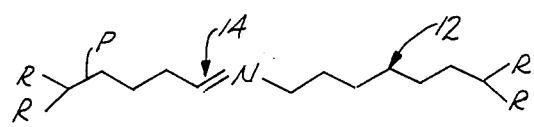

The invention relates to the use of pharmaceutically acceptable compositions which include effective amounts of hydroxy diphenylalkyl derivatives as the active ingredient for retarding the degenerative process of aging in mammals, particularly in man.

The term "aging" as used herein generally means any damage to the cells caused by toxic byproducts of oxygen metabolism. Such aging can, for example, result from partial damage or complete destruction of cells or from the conversion of imide bonds to amide bonds in human collagen and/or elastin resulting in hardening of the arteries or skin wrinkling, etc. Thus, the phrases "inhibiting aging" or "retarding aging" mean inhibiting or retarding damage to cells caused by toxic byproducts of oxygen metabolism.

The hydroxy diphenylalkyl derivatives useful in practice of principles of this invention may be represented by the following structural formula:

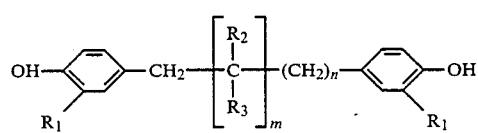

(1)

wherein
m is 0, 1 or 2;
n is 0 or 1;
R1 is hydrogen, halogen or hydroxy; and
R2 and R3 each independently represent hydrogen or methyl provided that when m is 0, n is 0 and when m is 1 or 2, n is 1 and R1 is hydroxy or halogen and that when m is 2, each R2 can be the same or different and each R3 can be the same or different.

Pharmaceutically acceptable salts of the compounds of formula (1) are also useful in practice of this invention. Furthermore, mixtures of compounds of formula (1) including the pharmaceutically acceptable salts may be used in accordance with practice of principles of this invention.

Preferred compounds of the formula (1) are bis(p-hydroxy-phenyl)methane and 1,4-bis(3,4-dihydroxy-phenyl)-2,3-dimethylbutane (nordihydroguairetic acid or NDGA).

If "m" is 3 or greater and/or if "n" is 2 or greater, the compound will not be transported as readily as desired through the mitochrondrial membranes. It is thought that the use of other antioxidant substances such as ethoxyquin, butylated hydroxytoluene (BHT), 2-mercaptoethylamine and methionine in place of the compounds of formula (1) is not desired. This is because the aforementioned antioxidants do not have as desirable a lipophilicity or zwitteron effect as do the compounds of formula (1). Therefore the compounds of formula (1) provided in accordance with this invention are transported more readily through the mitochondrial membranes than are the aforementioned antioxidants.

Preferably R1 is a halogen or hydroxy. Having a halogen or hydroxy at R1 tends to draw electron density to the R1 or halogen moiety. This reduces electron density over the entire phenyl ring, and in turn, reduces electron density on the hydroxy group adjacent to R1. The hydroxy adjacent R1 then becomes a relatively better electron "sink" or free radical electron acceptor which provides a highly deactivated phenol group which in turn tends to increase the efficiency of the molecule in scavenging cell-damaging radicals such as hydroxyl (.OH) radicals and other toxic byproducts of cell oxygen metabolism.

An important feature of the hydroxy diphenylalkyl derivatives set forth as being useful in accordance with practice of this invention, is that they have two highly deactivated phenol groups per molecule. None of the other known antioxidant substances previously disclosed by the literature to be useful as age retarding substances in various species have this feature.

The compounds of formula (1) are known and may be prepared according to methods disclosed in the literature from known materials. Such references include Lieberman et al, *Journal of Americal Chemical Society*, Vol. 69, pp 1540 (1947) and U.S. Pat. No. 2,644,822 issued 1953 to Pearl, both of which are incorporated herein by this reference. The pharmaceutically acceptable salts may be mono- or di-salts and include the alkali metal salts, in particular, the sodium and potassium salts and the alkaline earth metal salts, such as the magnesium and calcium salts. These salts may also be prepared by methods presently known in the art.

The effective age retarding amount of the active compounds of formula (1) are preferably administered topically or orally either alone or in admixture with conventional pharmaceutical carriers. The active compounds of formula (1) may, if desired also be administered in appropriate pharmaceutically acceptable carriers, intravenously, subcutaneously, intramuscularly and intracutaneously. They may be administered in such forms as creams, lotions, tablets, dispersible powders, granules, capsules, syrups and elixirs. The compositions may contain one or more conventional adjuvants, such as sweetening agents, flavoring agents, coloring agents and preserving agents.

Tablets may contain one or more compounds of the formula (1) in admixture with conventional pharmaceutically acceptable excipients, e.g. inert diluents, such as calcium carbonate, sodium carbonate, lactose, sorbitol and talc, granulating and disintegrating agents, e.g.

starch and alginic acid, binding agents, e.g. sorbitol, microcrystalline cellulose, gelatin and acacia, and lubricating agents, e.g. magnesium stearate, steric acid and talc. The tablets may be uncoated or coated by known techniques to delay disintegration and absorption in the gastrointestinal tract and thereby provide a sustained action over a longer period.

Creams and lotions may contain the active ingredient in admixture with conventional cosmetically (and pharmaceutically) acceptable excipients, e.g. moisturizers and humectants such as uric acid, reticulan, polymucosaccharides, hyaluronic acid and aloe vera. Similarly, oral liquids, e.g. suspensions may contain the active ingredients of formula (1) in admixture with any of the conventional excipients utilized for the preparation of such compositions, e.g. suspending agents (methylcellulose, tragacanth and sodium alginate) and wetting agents (lecithin, polyoxyethylene stearate and polyoxyethylene sorbitan mono-oleate). Capsules may contain the active ingredient of formula (1) alone or admixed with an inert solid diluent, e.g. calcium carbonate, calcium phosphate and kaolin.

Tablets, creams, lotions, oral liquids and capsules may all contain various preservatives. Examples of such preservatives are derivatives of butylated hydroxytoluene (BHT), butylated hydroxyanisole, methionine, cystein, ethoxyguin, ascorbic acid, tocopherol, catalase, superoxide dismutase, glutathione, glutathione peroxidase, 2-mercaptoethylamine, cystamine, benzoic acid, ethyl-o-hydroxybenzoate, ethylenediamine tetraacetic acid and all other mercaptans, thiols and disulfides. The pharmaceutical and cosmetic preparations provided in accordance with practice of principles of this invention may contain up to about 90% of the active ingredient of formula (1) in combination with the above described carriers or adjuvants.

The foregoing recitation of materials to be used in compositions containing compounds of formula (1) is presented for purposes of illustration and not limitation, it being understood that a variety of equivalent materials could also be used if desired.

DOSAGE

The effective oral dosage of the compounds of formula (1) employed for the retardation of aging, e.g. wrinkling of the skin and hardening of the arteries, may vary depending on the particular compound employed and the severity of the condition being treated. However, in general, satisfactory results are obtained when the compounds of formula (1) are administered to humans at a daily dosage of from about 0.5 mg to less then about 2 mg per kilogram (kg) of body weight; preferably given in divided doses two to six times a day, or in sustained release form. When the daily dosage of compounds of formula (1) is less than about 0.05 mg/kg of body weight the effect on preventing cell damage, i.e., inhibiting aging is only marginal. When the daily dosage of compounds of formula (1) is at about 2 mg/kg or greater the provision of such compounds becomes uneconomical. Further, such higher dosages are not required and may have an undesirable reverse effect, actually speeding up the aging process since the excess may upset the delicate balance of cell metastasis.

Dosage forms suitable for internal use comprise the active compound of formula (1) in either acid or salt form or mixtures thereof in intimate admixture with a solid or liquid which are pharmaceutically acceptable carriers or diluents. The preferred pharmaceutical compositions from the standpoint of preparation and ease of administration are solid compositions, hard-filled capsules or tablets containing from about 20 to 100 mg of active ingredient in acid or salt form.

EXAMPLE 1

Tablets suitable for oral administration in accordance with practice of this invention may be prepared by conventional pharmacological techniques and may contain the following ingredients. (While Nordihydroguairetic acid (NDGA) is shown in the Examples as the active ingredient, any compounds or mixture of compounds defined by the formula (1) could be used). Such tablets are useful in the retardation of biological aging of mammals.

| Ingredients | Weight |
|---|---|
| Nordihydroguairetic acid (NDGA) | 40 mg. |
| Sorbitol | 208 mg. |
| Magnesium Sterate | 2 mg. |

EXAMPLE 2

Dry filled capsules suitable for oral administration in accordance with practice of this invention which may contain the following ingredients are prepared in a conventional manner.

| Ingredients | Weight |
|---|---|
| Nordihydroguairetic acid (NDGA) | 80 mg. |
| Inert solid diluent used to insure good mechanical flow in filling capsules (lactose, sorbitol, starch, kaolin) | 170 mg. |

Examples of formulations for topical application provided in accordance with practice of this invention containing NDGA as the active ingredient are shown in examples 3 and 4 below:

EXAMPLE 3

| Ingredients | Composition % W/W |
|---|---|
| Nordihydroguairetic acid (NDGA) | 0.5 |
| Purified water | 88.0 |
| Butylene glycol | 1.0 |
| Octyl Palmitate | 1.0 |
| Aloe Vera extract | 1.0 |
| Glyceryl Sterate | 0.5 |
| Peg-100 Sterate | 0.5 |
| Ceteareth-20 | 0.5 |
| reticulan | 0.5 |
| Myristyl myristate | 0.5 |
| Mucopolyscaccharides | 0.5 |
| Jojoba oil | 0.5 |
| Collagen | 0.5 |
| Amino Acids | 0.5 |
| Paba | 0.5 |
| Vitamin A | 0.5 |
| Vitamin E | 0.5 |
| Allantoin | 0.5 |
| Imidazolidinyl urea | 0.5 |
| Carbomer 934 | 0.5 |
| Vitamin B-5 | 0.5 |
| Methyl-propylparaben | 0.2 |
| Tea | 0.1 |
| Vitamin D | 0.1 |
| Natural fragrance | 0.1 |

EXAMPLE 4

In Example 4 the composition of Part A is formulated separately from the composition of Part B and then Parts A and B are mixed together.

| Ingredients | Part A | % W/W |
| --- | --- | --- |
| Nordihydroguairetic acid (NDGA) | | 2.0 |
| Incroquant BTQ | | 1.0 |
| Crodacol CS-50 | | 0.5 |
| Super Sterol Ester | | 0.5 |
| Crodamol PMP | | 1.0 |
| Polawax | | 1.5 |
| Crosilk liquid | | 5.0 |

The ingredients listed under Part A of Example 4 are manufactured and distributed under their respective trademarks by Croda, Inc., New York, N.Y. "Volatile Silicone 03314" is manufactured and distributed by SWS Silicones Corporation, Adrian, Mich. and "GG Germaben II" is manufactured and distributed by Sutton Laboratories, Inc., Chatham, N.J.

Preferred compositions for topical administration contain from about 0.5% to about 20% by weight of the active ingredient of formula (1) in either acid or salt form. Since the compounds of formula (1) are active by themselves in retarding aging, i.e., in inhibiting damage to cells, they are comtemplated as the only "active ingredient" in the compositions provided in accordance with practice of principles of this invention. More preferably the compositions comprise from about 2% to about 5%. If the composition contains less than about 0.5% it will be only marginally effective and at greater than about 20% the economics would not be as favorable as desired and such high concentrations could possibly produce detrimental side effects. However, compositions for topical application where the active ingredient is in concentrations of from 0.001% to 90% by weight are contemplated.

Without being bound by theory, it is thought that the compositions described above when administered orally or topically, as described, inhibit oxidation of imide bonds between collagen or elastin fibers to amide bonds. This can be seen by referring to FIG. 1 where a pair of collagen fibers (or a pair of elastin fibers) 10 and 12 are shown schematically lying adjacent to each other. The fibers owe their elasticity to reversible bonds that bind them together chemically. The two active sites that provide the bonds are the —CHO and —NH$_2$ moieties. The fibers are shown bonded together by the reversible imide bond 14 at the bottom of FIG. 1. This imide bonding is caused by the uptake and giving off of water (H$_2$O) which is called hydration and dehydration. Because the imide bonds open and close continuously the collagen (or elastin) fibers glide freely past one another. This biochemical effect provides elasticity to the skin and arteries.

Figure 2:
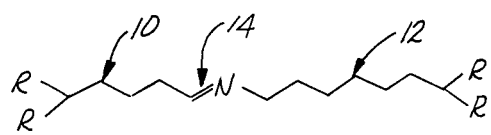
FIG. 2 is a schematic representation of two collagen fibers (R) or two elastin fibers (R) joined together by an amide bond which is further oxidized to a permanent amide bond.
Figure 2:
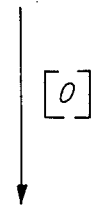
Figure 2:

Turning to FIG. 2 (at the top) there are shown (for purposes of illustration) the same two fibers 10 and 12 initially bonded together by the imide bond 14. The bond is shown encircled at 16 at the bottom of FIG. 2 after it has been oxidized to the amide bond.

Humans stop growing and maturing after 20-30 years. During aging, the skin and arteries of man and other mammals become increasingly inelastic. This inelasticity is largely the result of the oxidation of the imide bond to the amide bond as is shown in FIG. 2.

The amide bond is permanent and results in a permanent rigid linking between collagen and elastin fibers.

EXAMPLE 5

As previously indicated, the compounds of formula (1) are useful because they possess pharmacological activity in mammals including humans. In one aspect of practice of techniques of this invention, the compounds of formula (1) are useful in retarding the aging phenomena of skin wrinkling. In this example, twenty four (24) Uppsala mice were fed standard lab chow (provided by Anticimax of Södertalje, Sweden) containing 0.3 weight% NDGA ad libitum from the twelfth to thirty-sixth month of their lifespan. Six (6) control mice were fed ad libitum the same lab chow as the aforementioned 24 mice except that the chow did not contain NDGA.

The NDGA fed mice were visually more youthful and healthy at 26 months of age than control mice. The last remaining control mouse showed significant hair loss, pigmentation loss, poor eyesight and difficulty in movement as compared with the four NDGA fed mice that were also still living at this stage of the experiment.

Especially apparent was the greater skin wrinkling in control mice versus NDGA fed mice. This increased wrinkling is indicative of collagen and elastin hardening and cross-linking via the conversion of imide to amide bonds as discussed above.

EXAMPLE 6

Figure 3:
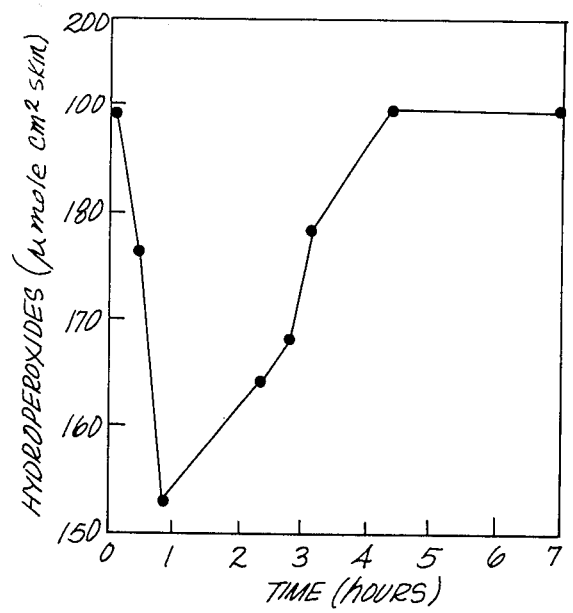
FIG. 3 is a graph showing the results of a double blind study set forth in Example 6, wherein a composition containing 2% NDGA by weight was applied topically to the skin of the foreheads of human volunteers.

Turning to FIG. 3, the results of a double-blind time study using a composition containing 2% by weight NDGA can be seen. This composition was the same as the composition set forth in Example 3 with the exception that the percentage of water was reduced to 86.5%. Starting at time zero, 10 milliliters of this cream was vigorously applied topically onto the skin of the forehead of a volunteer. Measurements were taken at different intervals using non-invasive, reflective, near-infrared spectroscopy. The methods of non-invasive, reflective, near infrared spectroscopy used in this example are set forth in detail in R. Lippman, "Rapid in vivo Quantification and Comparision of Hydroperoxides and Oxidized Collagen in Aging Mice, Rabbits and Man", *Experimental Gerontology*, Vol. 20, pp. 1-5, 1985, which is incorporated herein by this reference. Results showed that lipid hypdroperoxides in the other skin layers and microvascularization decreased from about 190 to 151 micromole/cm$^2$ skin after about one hour. The pharmacokinetics of topical NDGA application showed a gradual return to a normal level of 190 micromole/cm$^2$ level after approximately 4 hours. This experiment showed that facial skin and skin unsaturated lipids are preserved, and damage is prevented by applying NDGA according to the procedure of this example.

EXAMPLE 7

Glial cells from a human brain were cultivated by monolayering on Petri dishes. Cellular ATP production was measured using bioluminescent methods (luciferin, luciferase and photomultiplier detection). NDGA was added to various cultures to a level of 0.5% w/v and an increase in steady state ATP production was observed.

EXAMPLE 8

Mitrochondria from a human liver were freshly isolated and maintained in a culture environment so that normal respiration and ATP production occurred. Special chemical probes, e.g. luminol-carnitine derivatives, were pipetted into the mitochondria culture media. Uptake of the probes occurred in the mitochondrial inner membrane where oxygen metabolism and toxic oxygen byproducts are produced. The probes emitted chemiluminescent light in proportion to superoxide ($O_2^-$.) and hydroxyl radicals (.OH). This light was measured by a photomultiplier, and the results were quantified and recorded. NDGA added to the mitochondria in latter experiments significantly reduced the steady state light, and therefore, NDGA significantly reduced toxic oxygen byproducts and increased mitochondrial metabolic efficiency. Increased lifespan of the human mitochondria was also observed to occur.

EXAMPLE 9

Figure 4:
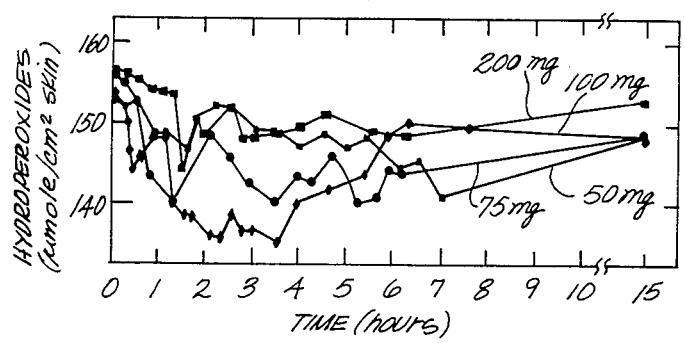
FIG. 4 is a graph showing the results of a pharmacokinetic time course study wherein single NDGA doses of 50 mg, 75 mg, 100 mg and 200 mg were administered to human volunteers in a double blind study.

Turning to FIG. 4 a graph of results of a pharmacokinetic time-course (double-blind) study of single doses of NDGA given to human volunteers at time zero is shown. Single doses of NDGA of 50 mg, 75 mg, 100 mg and 200 mg were given to volunteers who had fasted at least 12 hours (overnight). Placebos were given to two (2) other volunteers. Using the above referenced non-invasive technique called reflective, near-infrared spectroscopy, changes in the microvascular concentrations of lipid hydroperoxides were monitored during 8 hour test periods. The graph of FIG. 4 plots the concentration of hydroperoxides in the skin in micro mole/cm$^2$ on the vertical axis (as measured by the near-infrared spectroscopy technique) vs. time in hours on the horizontal axis. Subjects received single doses of NDGA and placebos orally, respectively.

The results, as can be seen in FIG. 4, show that NDGA was absorbed into the blood stream after about 1 to 2 hours upon oral administration into an empty stomach. NDGA reduced levels of microvascular lipid hydroperoxides at least 15% during the 4 to 8 hour study periods. A nearly flat line at approximately 150 micromole/cm$^2$ (not shown on the graph) was recorded for the two volunteers who received placebos. It is concluded that NDGA is an effective neutralizer of toxic byproducts of oxygen metabolism, i.e. lipid hydroperoxides, when taken at regular intervals of at least 6 hours, 3 times daily.

The above descriptions of exemplary embodiments of the methods and compositions for retarding aging, i.e., inhibiting damage to cells in mammals caused by toxic byproducts of oxygen metabolism, are for illustrative purposes. Because of variations which will be apparent to those skilled in the art, the present invention is not intended to be limited to the particular embodiments described above. The scope of the invention is defined in the following claims.

What is claimed:

1. A method for retarding aging in humans by administering to a human a daily dosage of from about 0.5 mg per kilogram of body weight to less than about 2 mg per kilogram of body weight of a pharmaceutically acceptable composition comprising a compound or a mixture of compounds represented by the following structural formula:

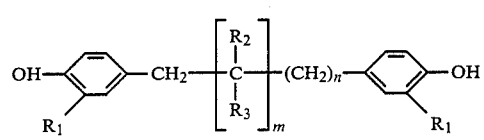

(1)

wherein
m is 0, 1 or 2;
n is 0 or 1;
R1 is hydrogen, halogen or hydroxy; and
R2 and R3 each independently represents hydrogen or methyl provided that when m is 0, n is 0 and when m is 1 or 2, n is 1 and R1 is hydroxy or halogen and that when m is 2, each R2 can be the same or different and each R3 can be the same or different or
a pharmaceutically acceptable alkali or alkaline earth metal salt thereof.

2. The method according to claim 1 wherein the compound is nordihydroguairetic acid.

3. The method according to claim 1 wherein the compound is bis(p-hydroxyphenyl)methane.

4. The method according to claim 1 wherein the composition is administered orally.

5. The method according to claim 1 wherein the composition is administered by a means selected from the group consisting of intravenously, subcutaneously, intramuscularly and intracutaneously.

6. A pharmaceutical composition in solid dosage form for retarding aging in humans consisting essentially of a compound or mixture of compounds represented by the following structural formula as the active ingredient:

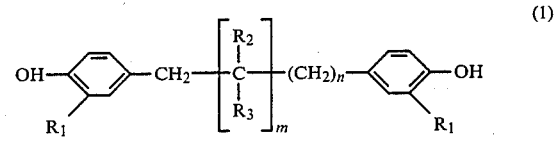

(1)

wherein
m is 0, 1 or 2;
n is 0 or 1;
R1 is hydrogen, halogen or hydroxy; and
R2 and R3 each independently represents hydrogen or methyl provided that when m is 0, n is 0 and when m is 1 or 2, n is 1 and R1 is hydroxy or halogen and that when m is 2, each R2 can be the same or different and each R3 can be the same or different or
a pharmaceutically acceptable alkali or alkaline earth metal salt thereof, wherein from about 20 mg to 100 mg of said active ingredient is present in the composition.

7. A composition as is claimed in claim 6 wherein the compound is nordihydroguairetic acid.

8. A composition as is claimed in claim 6 wherein the compound is bis(p-hydroxyphenyl)methane.

9. A pharmaceutical composition for topical administration to the skin of a human consisting essentially of an effective amount of a compound or mixture of compounds represented by the following structural formula as the only active ingredient in a topical pharmaceutically acceptable carrier:

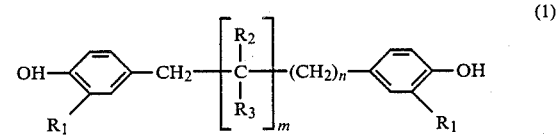

(1)

wherein
m is 0, 1 or 2;

n is 0 or 1;

R1 is hydrogen, halogen or hydroxy; and

R2 and R3 each independently represents hydrogen or methyl provided that when m is 0, n is 0 and when m is 1 or 2, n is 1 and R1 is hydroxy or halogen and that when m is 2, each R2 can be the same or different and each R3 can be the same or different or a pharmaceutically acceptable alkali or alkaline earth metal salt thereof.

10. A composition as is claimed in claim 9 wherein the compound is nordihydroguairetic acid.

11. A composition as is claimed in claim 9 wherein the compound is bis(p-hydroxyphenyl)methane.

12. A composition as is claimed in claim 10 wherein the composition contains from about 0.5% to about 20% by weight of nordihydroguairetic acid compared to the total weight of the composition.

13. A pharmaceutical composition for topical administration to the skin of a human consisting essentially of a compound or mixture of compounds represented by the following structural formula as the acitve ingredient in a topical pharmaceutically acceptable carrier, wherein the composition contains from about 0.5% to about 20% by weight of the active ingredient compared to the total weight of the composition:

$$OH-\phenyl(R_1)-CH_2-\left[\underset{R_3}{\overset{R_2}{C}}\right]_m-(CH_2)_n-\phenyl(R_1)-OH \quad (I)$$

wherein m is 0, 1 or 2;

n is 0 or 1;

R1 is hydrogen, halogen or hydroxy; and

R2 and R3 each independently represents hydrogen or methyl provided that when m is 0, n is 0 and when m is 1 or 2, n is 1 and R1 is hydroxy or halogen and that when m is 2, each R2 can be the same or different and each R3 can be the same or different or a pharmaceutically acceptable alkali or alkaline earth metal salt thereof.

14. A composition as is claimed in claim 13 wherein the compound is nordihydroguairetic acid.

15. A composition as is claimed in claim 13 wherein the compound is bis(p-hydroxyphenyl)methane.

16. A composition as is claimed in claim 14 wherein the composition contains from about 0.5% to about 20% by weight of nordihydroguairetic acid compared to the total weight of the composition.

* * * * *

UNITED STATES PATENT AND TRADEMARK OFFICE

CERTIFICATE EXTENDING PATENT TERM
UNDER 35 U.S.C. § 156

PATENT NO.:     4,695,590

DATED:          September 22, 1987

INVENTOR(S):    Richard D. Lippman

PATENT OWNER:   Block/Chemex, G.P.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

712 DAYS with all rights pertaining thereto as provided by 35 U.S.C. § 156(b).

I have caused the seal of the Patent and Trademark Office to be affixed this 6th day of December 1993.

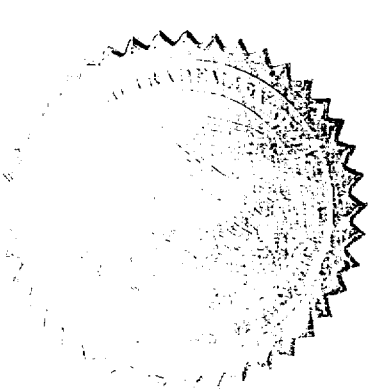

Bruce A. Lehman
Assistant Secretary of Commerce and
Commissioner of Patents and Trademarks